(12) United States Patent
Wils et al.

(10) Patent No.: US 7,932,238 B2
(45) Date of Patent: Apr. 26, 2011

(54) ANTI-INFLAMMATORY AND/OR ANALGESIC COMPOSITION FOR THE INTESTINE COMPRISING BRANCHED MALTODEXTRINS

(75) Inventors: Daniel Wils, Morbecque (FR); Laëtitia Deremaux, Lille (FR); Marie-Hélène Saniez, Lille (FR)

(73) Assignee: Roquette Freres, Lestrem (FR)

( * ) Notice: Subject to any disclaimer, the term of this patent is extended or adjusted under 35 U.S.C. 154(b) by 228 days.

(21) Appl. No.: 11/911,875

(22) PCT Filed: Apr. 4, 2006

(86) PCT No.: PCT/FR2006/000736
§ 371 (c)(1),
(2), (4) Date: Dec. 11, 2007

(87) PCT Pub. No.: WO2006/111624
PCT Pub. Date: Oct. 26, 2006

(65) Prior Publication Data
US 2008/0182821 A1    Jul. 31, 2008

(30) Foreign Application Priority Data

Apr. 18, 2005    (FR) .................................... 05 03852

(51) Int. Cl.
*A61K 31/715*    (2006.01)
(52) U.S. Cl. .............................. 514/58; 514/54; 536/103
(58) Field of Classification Search .................. 514/58, 514/54; 536/103
See application file for complete search history.

(56) References Cited

U.S. PATENT DOCUMENTS

| | | | |
|---|---|---|---|
| 6,630,586 B1 * | 10/2003 | Fouache et al. | 536/103 |
| 6,737,414 B2 * | 5/2004 | Saniez | 514/58 |
| 7,138,154 B2 * | 11/2006 | Brendel et al. | 426/548 |
| 2002/0182299 A1 | 12/2002 | Serpelloni | |
| 2003/0039740 A1 | 2/2003 | Saniez | |
| 2003/0077368 A1 | 4/2003 | Serpelloni | |
| 2004/0030151 A1 | 2/2004 | Zhuang et al. | |
| 2004/0058055 A1 | 3/2004 | Delebarre | |

FOREIGN PATENT DOCUMENTS

EP    1 245 578 A1    10/2002
GB    2 363 713 A    1/2002

OTHER PUBLICATIONS

International Search Report of PCT/FR2006/000736, date of mailing Oct. 25, 2005.
French M. A. et al., "Polyunsaturated Fat in the Diet May Improve Intestinal Function in Patients with Crohn's Disease", Biochimica Et Biophysica Acta. Molecular Basis of Disease, Amsterdam, NL, vol. 1360, No. 3, May 24, 1997, pp. 262-270.

* cited by examiner

*Primary Examiner* — Shaojia Anna Jiang
*Assistant Examiner* — Michael C Henry
(74) *Attorney, Agent, or Firm* — Young & Thompson

(57) ABSTRACT

The invention concerns a fiber-enriched anti-inflammatory and/or analgesic composition for the intestine, characterized in that it comprises branched maltodextrins having between 15 and 35% of glucoside bonds, 1 to 6, a reducing sugar content less than 20%, a polymolecularity index less than 5 and a number molecular weight Mn not more than 4500 g/mole.

24 Claims, No Drawings

ANTI-INFLAMMATORY AND/OR ANALGESIC COMPOSITION FOR THE INTESTINE COMPRISING BRANCHED MALTODEXTRINS

The invention relates to a fiber-enriched anti-inflammatory and/or analgesic composition for the bowel, characterized in that it comprises branched maltodextrins.

Chronic inflammatory bowel diseases (or IBDs) include in particular two distinct conditions: ulcerative colitis (UC) and Crohn's disease. These two diseases, which are both distinct and related, are characterized by more or less diffuse inflammatory lesions of the bowel, in particular due to a state of hyperactivation of the immune system of the bowel, the cause of which is unknown.

Their expression is essentially in the digestive system, with diarrhea, abdominal pain, loss of weight, and tissue inflammation.

The frequency of IBDs has been increasing over the past few decades. This is partly explained by the technical progress made, allowing the diseases to be more readily diagnosed, but it especially appears that the change in dietary habits is involved in the evolution of these diseases, just like food allergies, obesity and other "diseases of civilization".

For some time, there has been considerable interest in the combination of suitable diets with more conventional therapeutic treatments.

Prebiotics and probiotics are more particularly studied for being part of the dietetics of individuals affected by these pathologies, making it possible to improve their quality of life and to play an important role with regard to the preventive aspect of these disorders.

More particularly, it is recognized that the introduction of appropriate fiber into the diet has a beneficial effect on the health, this fiber exerting a protective effect in inflammations of the colon.

This fiber is generally divided up into two categories: soluble fiber and insoluble fiber.

Soluble fiber, such as pectin and inulin, which cannot be digested by the enzymes in humans, is fermented by the intestinal bacterial flora. This fermentation releases short-chain fatty acids in the colon, the effect of which is to reduce the pH thereof and, consequently, to limit the development of pathogenic bacteria.

Insoluble fiber, such as cellulose, resistant starches, corn fiber (spent grain) or soya fiber, has an essentially mechanical role in the gastrointestinal tract. It is only very slightly fermented by the intestinal flora and contributes to reducing the intestinal transit time through a ballast effect.

It results from the numerous studies tending to demonstrate the importance of the diet in the prevention of colon inflammation, that a relationship exists between complex sugars (polysaccharides, starch) and good colon physiology.

It is, in particular, the resistant starches, which are not digested in the small intestine, which are of great value for the health of the colon.

However, a lot of work remains to be accomplished in order to modify the resistant-starch composition of foods without changing the organoleptic properties thereof.

Since 1997, Kanauchi et al. have described the effects of food products based on germinated barley on colitis or diarrhea induced in laboratory animals (in *Biosci. Biotech. Biochem.* 1997, 61, 449-454 and in *J. Gasteroenterol.* 1998, 33, 179-188).

However, over the past few years, the specialists in these pathologies have turned rather toward "colonic foods", and more particularly prebiotics.

These prebiotics are defined as fertilizers for bacteria beneficial for the health which colonize the colon.

Prebiotics are functional ingredients present in many edible plants and in many food products.

The compounds conventionally categorized as prebiotics are fructooligosaccharides and transgalactooligosaccharides, but also lactulose, isomaltooligosaccharides, oligosaccharides extracted from soya, xylooligosaccharides, etc.

The targets of their functional effects are the colonic flora which ferment them and for which they serve as specific and selective substrates, the gastrointestinal physiology, and in particular the functions performed by the large intestine, the immune system, the bioavailability of minerals, and lipid metabolism.

Among the beneficial colonic flora whose growth is promoted by prebiotics, mention is especially made of bifidobacteria and lactobacilli.

Lactobacilli have the advantage of bringing about a reduction in the pH of the medium by the production of lactic acid, this reduction in pH preventing the growth of pathogenic flora such as proteobacteria or enterobacteria, which are causal agents of pathologies such as Crohn's disease or certain forms of ulcerative colitis.

Bifidobacteria are in particular described for their production of enzymatic activities of glucosidase type, which promote the release of flavonoids having anti-mutagenic and antioxidant effects.

Inflammatory diseases and the respective treatment thereof are the subject of active research. Experimental models of induction of colitis have been developed, such as the induction of colitis through the administration of a solution containing an allergen (TriNitroBenzene Sulfonate or TNBS) in ethanol in laboratory rats or mice.

The ethanol makes it possible to destroy the barrier formed by the intestinal mucosa and thus promotes penetration of the TNBS into the intestinal wall, this TNBS causing acute, often transmural, necroses, probably due to oxidative damage.

This model is envisioned for studies of localized hypersensitivity of the colon, and is particularly suitable due to the fact that the inflammations caused by this model are sensitive to the medicaments administered in the case of IBDs.

Several anti-inflammatory compositions for the bowel have been proposed and tested by virtue of this animal model.

Fructooligosaccharides (FOSs) are polymers of short-chain fructose units which are not hydrolyzed in the small intestine in humans, but are degraded by the resident flora of the colon.

FOSs mainly induce the growth of endogenous lactobacilli and bifidobacteria of the bowel in humans and animals.

In addition, FOS fermentation induces a decrease in the pH of the colon, induces the production of volatile fatty acids and lactates, and secondarily increases the production of butyrates.

In their review published in 2003 in the *American Society for Nutritional Sciences*, vol 133, 21-27, C. Cherbut et al. describe the preventive effect of FOSs in the bowel inflammation induced by TNBS in laboratory rats.

The protective effects of FOSs are measured by monitoring of the macroscopic score for colon damage (visual search for necroses and ulcers caused by the TNBS) and measurement of the myeloperoxidase activity (specific enzyme of polymorphonuclear neutrophil granules, marker for bowel inflammation).

It is thus shown in this article that FOSs significantly reduce bowel inflammation, making it possible to limit the damage in the bowel (necroses and ulcers), decrease myeloperoxidase activity and also decrease the weight loss induced by TNBS.

Moreover, C. Cherbut et al. also demonstrate that FOSs indeed have a prebiotic effect, i.e. are capable of stimulating the intestinal growth of beneficial bacteria in the colon, in the case in point lactic acid bacteria and butyric acid bacteria, which results in a decrease in the pH of the colon.

The mechanism of protection of FOSs is not clearly explained.

It has been proposed, in patent application US 2004/0219157, that FOSs stimulate the homeostasis of nonspecific immunological parameters and stimulate the growth of lymphocyte subpopulations.

It is also assumed that lactic acid bacteria, the growth of which is stimulated by FOSs, are antagonists of pathogenic bacteria, of which they block the development through the production of antimicrobial substances and by reducing the pH of the colon.

Lactic acid bacteria can also adhere to the intestinal walls and thus prevent colonization by these same pathogenic bacteria.

Moreover, FOSs also act on the decrease in the pH of the colon through the induced production of lactic acid and butyric acid.

However, this intestinal acidosis effect does not have only advantages.

In international patent application WO 04/026316, it is in fact described that this acidosis, particularly promoted by the growth of lactic acid bacteria, ultimately causes an erosion of the colonic mucosa, increasing the risk of ulcerative colitis.

Moreover, the accumulation of lactic acid in the colon can also result in the release of excess amounts in the blood, thus causing metabolic acidosis.

Inulin, but also FOSs, have the drawback of being fermented too rapidly in the colon, and can thus lead to imbalances in the microbial population which are detrimental to their protective effect on the colon.

In order to counterbalance this harmful effect, it is proposed, in said patent application WO 04/026316, to combine with the FOSs a polysaccharide characterized by its slow fermentation in the colon, in the case in point polydextrose.

Polydextrose is synthesized by random polymerization of glucose in the presence of sorbitol and of an appropriate acidic catalyst (such as citric acid) and at high temperature.

Polydextrose is widely used in nutrition as a bulking agent and as a low-calorie ingredient. Polydextrose is neither digested nor absorbed in the small intestine and a considerable portion is found in the feces.

Patent application WO 04/026316 especially teaches the use of polydextrose for preventing the acidosis effects induced by the imbalances caused in the microbial population of the colon, in particular by those induced by prebiotic agents such as inulin and FOSs.

Polydextrose is thus thought to promote the consumption of lactic acid by specific flora, counterbalancing its overproduction induced by FOSs.

It results from all the above that, to the applicant company's knowledge, no single polysaccharide composition exists which meets all the requirements of an effective protective composition for the bowel.

The objective of the present invention is therefore to remedy the drawbacks of the prior art.

The applicant company has thus found that the incorporation of branched maltodextrins advantageously makes it possible to reconcile all the objectives that up until now have been reputedly irreconcilable, by imagining and developing, at the cost of numerous research studies, a novel fiber-enriched anti-inflammatory and/or analgesic composition for the colon, which satisfies all the abovementioned criteria, namely a protective effect on the colonic mucosa, a moderate reduction in the pH of the colon, and a favored production of propionic and butyric acid bacteria, and, to a lesser extent, of lactic acid bacteria.

A subject of the invention is therefore branched maltodextrins having between 15% and 35% of 1→6 glucosidic linkages, a reducing sugar content of less than 20%, a polymolecularity index of less than 5 and a number-average molecular mass Mn at most equal to 4500 g/mol, for their use in a method of therapeutic treatment of the human or animal body.

For the purpose of the invention, the term "branched maltodextrins" is intended to mean the maltodextrins described in patent EP 1.006.128, of which the applicant company is the proprietor.

All the compositions of branched maltodextrins described in patent EP 1.006.128 are suitable for the preparation of anti-inflammatory and/or analgesic compositions for the bowel according to the invention.

According to a preferred variant, said branched maltodextrins have a reducing sugar content of between 2% and 5%, and a number-average molecular mass Mn of between 2000 and 3000 g/mol.

The branched maltodextrins have a total fiber content of greater than or equal to 50% on a dry basis, determined according to AOAC method No. 2001-03 (2001).

A subject of the invention is a fiber-enriched composition for the therapeutic treatment of the human or animal body, characterized in that it comprises the branched maltodextrins as active ingredient.

The fiber-enriched anti-inflammatory and/or analgesic composition for the bowel according to the invention comprises 0.5% to 20%, preferably 5% to 10% by dry weight of said branched maltodextrins so as to constitute a sufficient supply of fiber and protective effect for the colon.

Below 0.5% by weight of branched maltodextrins in the anti-inflammatory and/or analgesic composition for the bowel in accordance with the invention, the supply of fiber is insufficient to have a detectable effect.

These branched maltodextrins have an indigestibility characteristic which results in their assimilation in the small intestine being prevented.

They provide a source of indigestible fiber beneficial for the metabolism and for the intestinal equilibrium.

Their high content of 1-6 glucosidic linkages in fact confers on them prebiotic properties which are entirely specific: it has in fact emerged that butyrogenic, lactic acid or propionic acid bacteria metabolize these highly branched compounds.

These branched maltodextrins also promote the development of bifidogenic bacteria, to the detriment of undesirable bacteria, and thus also promote the expression of α- and β-glucosidase activities.

The anti-inflammatory and/or analgesic composition for the bowel in accordance with the invention makes it possible to stimulate by a factor of 2 to 10, preferably 3 to 8, the α- and β-glucosidase enzymatic activities of the caecal content and of the stools, as will be exemplified hereinafter.

This results in properties which are entirely beneficial to the health of the consumer.

Furthermore, the consumption of the branched maltodextrins of the anti-inflammatory and/or analgesic composition in accordance with the invention by the microorganisms of the colon will result in the pH of the cecal, intestinal and fecal content being reduced by 0.5 to 1 unit, thereby reflecting a balanced growth of said microorganisms.

The use of the anti-inflammatory and/or analgesic composition according to the invention also makes it possible to increase the production of volatile organic acids in the cecum, which organic acids are chosen from the group consisting of acetic acid, butyric acid and propionic acid, preferably propionic acid and butyric acid.

The protective effect on the colonic mucosa is demonstrated in particular in animals after administration of TNBS and is reflected by notable results, as will be exemplified hereinafter.

The animals continue to feed normally, and are significantly protected against the necrosing inflammation induced by TNBS, as demonstrated by the decrease in myeloperoxidase (or MPO) activity, assayed in the intestinal epithelium.

In fact, this MPO activity reflects the infiltration of neutrophils into the phagosomes and the extracellular space, and makes it possible to quantify the inflammatory process with which it is directly correlated.

The anti-inflammatory and/or analgesic composition for the bowel in accordance with the invention therefore makes it possible to reduce by from 5% to 40%, preferably from 7% to 35%; the myeloperoxidase activity of the intestinal epithelium.

This effect significantly reflects the protective effect of said compositions against bowel inflammation, making it possible to envision the preparation of anti-inflammatory and/or analgesic compositions for the bowel which improve the well-being of the patients, both in humans and animals.

It has, furthermore, been found that the branched maltodextrins according to the invention do not generate osmotic diarrhea, even at large doses.

The osmotic diarrhea phenomenon is observed when low-molecular-weight fermentable carbohydrates, such as, for example, lactulose and fructooligosaccharides, are consumed.

This phenomenon is reflected by an increase in the water content of the stools in reaction to an increase in the osmolarity of the fecal content, it being possible for this increase in water content to go as far as the appearance of diarrhea. Surprisingly and unexpectedly, the branched maltodextrins in accordance with the invention do not cause this phenomenon although they are fermentable.

In the diet, the anti-inflammatory and/or analgesic composition for the bowel in accordance with the invention can be in a ready-to-use form, or else in the form of a drink, such as a fruit juice, a soup, or else in the form of yogurts or incorporated into breakfast cereals.

Said composition can, moreover, be used in animals, and more particularly in cats, dogs, pigs, rabbits or the other farm animals which are sensitive to bowel inflammation, animals with a decreased immunity.

This composition can also be proposed for supplementing the diet of individuals suffering from IBDs, but also for individuals suffering from irritable bowel syndrome, and individuals suffering from traveler's diarrhea, and abdominal pain of which the etiology is often unknown.

In terms of pharmacy, an anti-inflammatory and analgesic composition for the bowel in accordance with the invention can comprise the branched maltodextrins and at least one other active ingredient, in a proportion which depends on the nature of the active ingredient under consideration.

This other active ingredient is preferably an anti-inflammatory agent for the bowel.

In the treatment of IBDs, for example, two types of treatments can be proposed:

a treatment using medicaments derived from salicylated compounds, for instance sulfasalazine or its derivatives, such as 5-aminosalicylates (5-ASA), a treatment based on medicaments of the corticoid family, such as cortisone or prednisolone.

One embodiment of the invention relates to a composition as described above comprising the branched maltodextrins, characterized in that it also comprises at least one active ingredient chosen from the group consisting of sulfasalazine and its derivatives and corticoids.

According to a specific embodiment, the invention relates to a composition as described above comprising the branched maltodextrins, also comprising an active ingredient chosen from the group consisting of sulfasalazine and its derivatives, characterized in that the ratio by weight of branched maltodextrins to weight of sulfasalazine or of one of its derivatives is between 2 and 30.

A specific embodiment of the invention relates to a composition as described above comprising the branched maltodextrins, also comprising an active ingredient chosen from the group consisting of corticoids, characterized in that the ratio by weight of branched maltodextrins to weight of corticoid is between 2 and 250.

Typically, a composition according to the invention can be in the form of a liquid, a powder, a syrup, a suppository, a tablet or a lozenge.

One embodiment of the invention relates to a kit for the therapeutic treatment of the human or animal body, comprising:

a) a first composition as described above comprising the branched maltodextrins; and b) a second composition comprising an anti-inflammatory agent for the bowel.

One embodiment of the invention is a method for treating or preventing bowel inflammations and/or calming bowel pain, comprising the administration to an individual of a sufficient therapeutic amount of branched maltodextrins.

A specific embodiment of the invention is a method for treating or preventing bowel inflammations and/or calming bowel pain, comprising the administration to an individual or to an animal of a composition as described above comprising the branched maltodextrins.

The compositions described above comprising branched maltodextrins may advantageously be administered to an individual or to an animal in combination with a second composition comprising an anti-inflammatory agent for the bowel. During the treatment, the two compositions may be administered concomitantly or sequentially over time. The method of administration of the second composition depends on the anti-inflammatory agent for the bowel that is used.

A specific embodiment of the invention is a method for treating or preventing bowel inflammations and/or calming bowel pain, comprising the administration of the two compositions described in the kit described above, concomitantly or sequentially over time.

One embodiment of the invention is the use of branched maltodextrins for the manufacture of a composition or of a kit for treating or preventing bowel inflammations and/or calming bowel pain.

Among the diseases and the pain that can be treated or prevented, mention may be made of chronic inflammatory bowel disease, irritable bowel syndrome, traveler's diarrhea or abdominal pain. Among the chronic inflammatory bowel diseases, mention may be made of ulcerative colitis and Crohn's disease.

As regards the analgesic role of the composition of the invention, it is estimated with regard to the expression of PPARγ and MOR receptors.

PPARγs (or Peroxisome Proliferator Activated Receptors γ) are part of the family of nuclear receptors. They are in particular activated by fatty acids and are involved in the transduction of metabolic and nutritional signals in transcriptional responses. They play a major role in maintaining the integrity of the intestinal mucosa.

It is known to those skilled in the art that PPARγs are greatly involved in the regulation of inflammation of the colon. They are also expressed in the case of colon cancers and their activation inhibits cell growth and cell differentiation.

MORs (or Opioid Receptor) are found in the central and peripheral nervous systems and can be present in particular in the colon. The principal function of MORs is the analgesic function. The second function is the inhibition of intestinal mobility. MORs are also involved in the regulation of bowel inflammation.

As will be exemplified hereinafter, it is remarkable to note that the composition of the invention makes it possible to increase the activity of the peroxisome proliferator activated receptor γ (PPAR-γ) by a factor of 1.2 to 3, preferably by a factor of 1.6 to 2.

Similarly, the composition of the invention makes it possible to increase the number of μ Opioid Receptors (MORs) by a factor of 1.2 to 10, preferably by a factor of 2.5 to 7.5, even more preferably by a factor of 4 to 5.

Finally, said composition is particularly suitable for stressed individuals in whom the stress manifests itself at the level of the bowel.

The invention will be understood more clearly upon reading the following examples which are illustrative and nonlimiting.

Example 1

Laboratory rats were used to study the effect, in their food, of the compositions comprising branched malto-dextrins of the invention (MDB) or glucose (control) combined with insoluble fiber (spent corn grain or cellulose) with respect to the protection of their colonic mucosa after administration of TNBS.

The insoluble fiber (in the case in point spent corn grain) and the MDBs of the invention are combined so as to mimic the fiber intake from cereal products in the diet according to the recommendations of the health authorities.

In addition, the spent corn grains were chosen for their richness in terms of carotenoids and polyphenols (in particular in terms of phenolic acid and ferulic acid).

The branched maltodextrins of the invention selected in this example have between 15% and 35% of 1→6 glucosidic linkages, a reducing sugar content of between 2% and 5%, a polymolecularity index of less than 5 and a number-average molecular mass Mn of between 2000 and 3000 g/mol:

| Reducing sugars | 2.3 |
| Mn (g/mol) | 2480 |
| Mw (g/mol) | 5160 |
| 1,2-linkage (%) | 10 |
| 1,3-linkage (%) | 12 |
| 1,4-linkage (%) | 49 |
| 1,6-linkage (%) | 29 |

They also have a total fiber content of 90% on a dry basis, determined according to the AOAC method (No. 2001-03).

64 OFA rats of Sprague Dawley origin are divided up into 8 groups which each receive, in their food and in their drink, a specific diet whose composition is given in the following Table I.

The glucose and the branched maltodextrins are present in the drink of the nutritional intake in a proportion of 5% weight/weight. The cellulose and the spent grains are present in the food of the nutritional intake in a proportion of 5% weight/weight.

TABLE I

| Group | Product tested in the drink | Product tested in the food | Intrarectal injection |
|---|---|---|---|
| 1 | Glucose | Cellulose | NaCl |
| 2 | MDB | Cellulose | NaCl |
| 3 | Glucose | Spent grain | NaCl |
| 4 | MDB | Spent grain | NaCl |
| 5 | Glucose | Cellulose | TNBS |
| 6 | MDB | Cellulose | TNBS |
| 7 | Glucose | Spent grain | TNBS |
| 8 | MDB | Spent grain | TNBS |

After one week of quarantine, during which the animals receive standard food and drinking water, the rats consume the food and the drink according to the diet described in Table 1, for 20 days.

They are then made to fast for 24 hours.

At $D_{21}$, the animals are treated by intrarectal injection with the products specified in Table 1.

The animals of groups 5 to 8 receive an intrarectal injection of 500 μl of TNBS diluted in ethanol to 40% Gay Lussac, whereas groups 1 to 4 receive an intrarectal injection of 500 μl of NaCl at 9%.

The TNBS is injected at the dose of 10 mg/kg of bodyweight and per day.

This dose is known to produce a severe but reversible inflammatory reaction.

The change in the animals' weight is monitored over the 3 days following the injection.

At $d_{24}$, the animals are sacrificed by $CO_2$ asphyxia.

The animals are weighed and then, after autopsy, the colon is removed, emptied and then weighed.

It is subsequently observed with the naked eye and is assigned a Wallace score.

The myeloperoxidase (or MPO) activity is also assayed in the intestinal epithelium.

This activity reflects the infiltration in neutrophils into the phagosomes and the extracellular space, and makes it possible to quantify the inflammatory process with which it is directly correlated.

The Wallace score is established using the Wallace scale as shown in the following Table II.

TABLE II

| Score | Macroscopic observations |
|---|---|
| 0 | No damage. |
| 1 | Hyperemia. No ulcer. |
| 2 | Hyperemia and thickening of the mucosa. No ulcer. |
| 3 | An ulcer without thickening of the mucosa. |
| 4 | 2 or more sites of ulceration or of inflammation. |
| 5 | 2 or more sites of ulceration or of inflammation or a site of ulceration/inflammation extending |

TABLE II-continued

| Score | Macroscopic observations |
|---|---|
| | over more than 1 cm over the length of the colon. |
| 6 and + | If the damage covers more than 2 cm of the length of the colon, the score is increased by 1 for each additional cm of damaged tissue. |

As regards the assaying of the MPO activity, it requires the colon to be prepared according to the following protocol.

The fragments of colon are suspended in 6 ml of hexadecyltrimethylammonium bromide buffer (0.5% of HTAB in a 50 mM phosphate buffer, pH 7.0). The fragments thus treated are ground and homogenized using a Polytron for 10 s. Each sample is treated with ultra-sound using a Vibra Cell 500 watts device from Sonics and Materials Inc., Danbury, Conn., USA (converter power of 500 W, power dissipated at the probe of 30%—i.e. 150 W/cm$^2$, pulser in position 2 i.e. 66% of a second).

The sonicates subsequently undergo 3 cycles of freezing-thawing before again being treated with ultrasound under the same conditions. The samples are subsequently centrifuged for 15 min at 10 000 g at 4° C. The supernatant is recovered in order to assay the MPO. The determination of the MPO activity is based on oxidation of a hydrogen peroxide-dependent artificial hydrogen donor (guaïacol), which, in its oxidized form, becomes an orangey color.

The monitoring of the apparent density at 470 nm and at 30° C. gives the activity values (expressed as absorbance units/minute/gram of colon). All the results obtained are given in the following Tables III and IV (values expressed as the mean of the results of the measurements carried out on the 8 animals of each group ±standard deviation).

TABLE IV

| Batch | Wallace scores | Weights of the emptied colons (g) | MPO activities (absorbance units/min/g) |
|---|---|---|---|
| 1 | 0.0 ± 0.0 | 2.04 ± 0.30 | 0.126 ± 0.072 |
| 2 | 0.0 ± 0.0 | 2.19 ± 0.21 | 0.119 ± 0.084 |
| 3 | 0.0 ± 0.0 | 1.95 ± 0.39 | 0.154 ± 0.120 |
| 4 | 0.0 ± 0.0 | 1.96 ± 0.26 | 0.096 ± 0.047 |
| 5 | 5.8 ± 1.0 | 2.82 ± 0.48 | 3.152 ± 1.244 |
| 6 | 5.9 ± 2.0 | 2.90 ± 0.43 | 2.908 ± 1.330 |
| 7 | 6.5 ± 1.9 | 2.99 ± 0.73 | 2.685 ± 0.650 |
| 8 | 3.9 ± 2.7 | 2.76 ± 0.37 | 2.114 ± 1.639 |

This result is confirmed by the determination of the Wallace score. In fact, the animals having received the compositions in accordance with the invention with spent grain and TNBS have a Wallace score of 3.9, to be compared with the mean scores of 5.8, 5.9 and 6.5 obtained for the other groups having received TNBS.

This mean score of 3.9 indicates a significantly lower level of inflammation for the animals of group 8.

The results of the colon weight measurements show, first of all, that the animals having received an injection of TNBS have a heavier colon than the colon of the animals which were not treated with TNBS.

This phenomenon is in particular due to the edema which invades the mucosa of the inflamed colons.

The mean weight of the colon of the animals of group 8 remains high compared with the mean weight of the colons of the animals of the groups which did not receive TNBS, but it remains the lowest weight of all those of the groups of animals treated with TNBS.

As regards the measurements of the MPO activities, which were obviously low for the animals of the groups not treated

TABLE III

| Batch | D0 | D7 | D14 | D20 | D21 | D22 | D23 | D24 |
|---|---|---|---|---|---|---|---|---|
| 1 | 140.5 ± 7.4 | 199.6 ± 13.6 | 259.0 ± 19.6 | 308.2 ± 14.9 | 275.3 ± 15.4 | 301.5 ± 15.8 | 306.6 ± 15.8 | 316.6 ± 16.6 |
| 2 | 141.3 ± 4.9 | 204.1 ± 14.2 | 263.3 ± 14.1 | 313.2 ± 10.9 | 294.4 ± 45.4 | 301.7 ± 12.7 | 310.7 ± 13 | 320.9 ± 12.1 |
| 3 | 139.0 ± 7.1 | 199.2 ± 14.5 | 257 ± 17.7 | 312.6 ± 19.9 | 280.8 ± 18.8 | 310.1 ± 18.5 | 316.9 ± 18.6 | 327.1 ± 20.9 |
| 4 | 138.9 ± 4.6 | 199.1 ± 11.5 | 258.9 ± 17.2 | 305.6 ± 17.8 | 274.5 ± 16.7 | 299.2 ± 15.0 | 305.1 ± 16.0 | 315.3 ± 16.0 |
| 5 | 140.2 ± 10.3 | 200.6 ± 13.4 | 259.4 ± 14.5 | 305.8 ± 15.4 | 274.7 ± 14.8 | 275.9 ± 14.4 | 270.0 ± 13.0 | 276.8 ± 20.9 |
| 6 | 147.2 ± 9.3 | 211.4 ± 19.4 | 270.6 ± 23.8 | 317.3 ± 22.7 | 280.9 ± 22.1 | 288.5 ± 22.0 | 287.4 ± 26.6 | 296.6 ± 28.6 |
| 7 | 145.9 ± 14.6 | 208.8 ± 24.2 | 266.1 ± 31.7 | 314.7 ± 34.0 | 281.9 ± 31.2 | 285.4 ± 37.0 | 275.0 ± 38.8 | 286.7 ± 40.7 |
| 8 | 144.6 ± 13.7 | 208.1 ± 19.4 | 266.6 ± 18.2 | 319.1 ± 11.1 | 286.0 ± 13.6 | 297.3 ± 14.3 | 301.8 ± 15.0 | 312.5 ± 12.5 |

The weight evolution shows that, at $D_{20}$, all the animals have the same weight. At $D_{21}$, all the animals lose weight because they have been made to fast before the intrarectal injection.

At $D_{22}$, all the animals who have been treated with an intrarectal injection of 9% NaCl regain a significant amount of weight.

Group No. 8 is the only one having received an inflammation-triggering administration of TNBS whose weight evolution goes up from $D_{22}$.

The weight evolution of the animals of groups 5, 6 and 7 goes up moderately only from $D_{23}$ and $D_{24}$.

Since the weight curve for the animals of group 8 is identical to that for the animals which did not receive TNBS, this indicates that these animals began to feed again from $D_{21}$. These animals were therefore protected against the necrosing inflammation induced by TNBS.

with TNBS, it appears once again that it is group 8 which shows the least MPO activities compared with the other groups of animals treated with TNBS.

The animals of group 8 are therefore significantly protected against the necrosing inflammation induced by TNBS.

Example 2

Laboratory rats are used to study the effect of the branched maltodextrins of the invention (identical to those of Example 1) and of dextrose (control) on the colon irritation induced by the administration of TNBS in male Wistar rats, and on their cognitive performances in the aversive light stimulus avoidance conditioning test.

This test uses the rat's aversion to a brightly lit environment. The principle is that an animal which suffers is an animal which learns more slowly in the case of a conditioning test.

Firstly, the rat learns to control its aversive light environment in the case of operating conditioning: the animal learns to press an active lever (LA) in order to obtain periods of darkness of 30 seconds as positive reinforcement.

The device also comprises another lever which, when it is actuated, does not make it possible to obtain light: inactive lever (LI).

The total number of times the active and inactive levers are pressed makes it possible to evaluate the level of manipulatory activity of the rats.

The acquisition of the learning (discrimination between the two levers) is evaluated by comparing the number of times each of the two levers is pressed in the "light" phase (LA vs LI).

48 male Wistar/AF SPF rats are divided up into 4 groups which receive, in their nutritional intake, a diet made up as described in the following Table V.

TABLE V

| Group | Diet | Nature of the treatment at $D_{17}$ |
|---|---|---|
| 1 | Dextrose (5%) | Ethanol (20%) |
| 2 | Dextrose (5%) | TNBS - alcohol (20%) |
| 3 | MDB (5%) | Ethanol (20%) |
| 4 | MDB (5%) | TNBS - alcohol (20%) |

After a quarantine period during which the animals receive a standard food intake and drinking water, the animals consume a food supplemented either with 5% of branched maltodextrins of the invention, or with 5% of dextrose, for 15 days.

At $D_{15}$, the animals are made to fast for 48 hours.

At $D_{17}$, the rats are anesthetized and 2 out of 4 groups (groups 2 and 4) receive an intracolonic administration of 500 μl of TNBS-ethanol at 20% Gay Lussac, at a rate of 3 mg/kg of bodyweight (i.e. 1 mg per rat—this dose is recognized to induce pain associated with weak bowel irritation).

From $D_{17}$ to $D_{23}$, the animals continue to receive the diets supplemented with MDBs or with dextrose.

At $D_{22}$, a cognitive test is carried out: the aversive light stimulus avoidance test (ALSAT).

The following Tables VI and VII give the result of the ALSAT test applied to the animals of the various groups. Table VII gives the total number of presses over the course of the test.

TABLE VI

| | Groups | | | |
|---|---|---|---|---|
| | 1 | 2 | 3 | 4 |
| ANOVA F (3.41) = 0.77; N.S. | 39.33 ± 8.63 | 35.20 ± 9.43 | 40.08 ± 7.43 | 53.27 ± 9.72 |

Table VII gives the number of presses on the LAs and the LIs.

Although the results are not significantly different, Table VII shows that the rats having received the MDB of the invention in their diet press the levers more often, and more particularly group 4 with respect to group 2.

TABLE VII

| | Groups | | | |
|---|---|---|---|---|
| | 1 | 2 | 3 | 4 |
| Presses LA | 10.50 ± 1.79 | 9.60 ± 2.13 | 10.25 ± 1.45 | 12.45 ± 1.67 |
| Presses LI | 9.00 ± 2.20 | 8.20 ± 2.02 | 6.42 ± 1.19 | 7.64 ± 1.07 |
| Paired t test (bilat. prob.) (LA vs LI) significance | t = 0.73 N.S. | t = 1.63 N.S. | t = 4.60 P < 0.001 | t = 5.59 P < 0.001 |

According to Table VIII, only the animals having received the MDB of the invention, with or without TNBS, are capable of differentiating between the LA and the LI, by more significantly pressing the LA, thus demonstrating a positive effect of the product against the pain induced by the TNBS.

At $D_{23}$, the animals are sacrificed; the colon is removed and examined according to the score scale given in the following Table VIII.

TABLE VIII

| Colon score | Microscopic observation |
|---|---|
| 0 | No damage. |
| 1 | Localized hyperemia with no ulcer |
| 2 | Ulceration without significant inflammation |
| 3 | Ulceration with inflammation |
| 4 | Several sites of ulcers and of inflammations; size of ulcers <1 cm |
| 5 | Multiple sites of ulcers and of inflammations; size of ulcers ≧1 cm |

The colons removed from the 4 groups are fixed in Carson's liquid fixative and observed microscopically.

The following Table IX gives the score for the colons of said various groups.

TABLE IX

| | Groups | | | |
|---|---|---|---|---|
| | 1 | 2 | 3 | 4 |
| ANOVA F (3.41) = 3.89; P = 0.02 | 2.50 ± 0.42 | 2.10 ± 0.41 | 1.17 ± 0.30 | 1.00 ± 0.36 |

The statistical analysis (ANOVA) shows that the colon scores for group 3 are significantly less than those for the rats of group 1 and tend to be significantly less than those for group 2.

The colon scores for the rats of group 4 are also significantly less than those for group 1 and tend to be significantly less than those for group 2.

The following Table X gives the result of the examinations by microscopy carried out on the colons fixed in Carson's liquid fixative (macroscopic scores), expressed in average degree of enteropathy (inflammations and necroses/ulcerations).

TABLE X

|  |  | Group | | | |
|---|---|---|---|---|---|
|  |  | 1 | 2 | 3 | 4 |
| Inflammation | Incidence | 12/12 | 12/12 | 12/12 | 12/12 |
|  | average degree | 2.8 | 2.8 | 2.3 | 2.2 |
| Necroses/ulceration | Incidence | 11/12 | 9/212 | 12/12 | 12/12 |
|  | average degree | 2.9 | 3.1 | 2.2 | 1.7 |
| Inflammation + necrosis/ulcerations | Incidence | 12/12 | 12/12 | 12/12 | 12/12 |
|  | average degree | 2.8 | 2.8 | 2.2 | 1.9 |

The macroscopic scores of Table IX are lower when the animals receive the MDBs according to the invention, compared with the animals having received the dextrose (control animals).

This observation is well correlated with the microscopic observation, since the score of 1.9 was assigned to group 4, whereas it is 2.8 for group 2.

It can therefore be concluded that all the animals show inflammation, but with different degrees of severity.

The enteropathy is less severe when the animals have received the MDBs according to the invention, thereby confirming the macroscopic results previously stated.

These results are to be related to the learning test results demonstrating that the animals which showed better learning were protected against the pain induced by TNBS, demonstrating the analgesic nature of the composition according to the invention.

Example 3

The protective effect of the branched maltodextrins of the invention (those of Example 1) against bowel inflammation in piglets is studied by assaying blood haptoglobin.

Haptoglobin is a plasma glycoprotein ($\alpha 2$-globulin) synthesized by the liver, capable of binding hemoglobin. The haptoglobin content is measured by an immunological method using diagnostic kits accessible to those skilled in the art.

The blood haptoglobin content increases in inflammatory syndromes, irrespective of the cause. Its kinetics are slow, such that, if its level is high, this reflects the fact that the inflammation has been present for a certain amount of time.

In contrast, a decrease in its level in the blood reflects a protective effect on the inflammation.

The trial is carried out on one group of 128 weaned piglets weighing 7.2±1.04 kg at the beginning of the study, the group being divided up into 4 batches, each of 32 animals, of the same live weight and sex (16 castrated males and 16 females).

The experimental treatments are the following (for a total period of 77 days):

Batch No. 1: control animals fed with a conventional diet,
Batch No. 2: animals receiving the MDB according to the invention in a proportion of 2% by weight of the food,
Batch No. 3: animals treated medically since fed with a food containing two antibiotics (chlortetracycline and spiramycin) in a proportion of 1000 and 400 mg/kg, respectively, during the test period (14 d), then fed once again with a conventional diet during the remaining period of the trial (15-77 days),
Batch No. 4: animals treated medically since fed with a food containing two antibiotics (chlortetracycline and spiramycin) in a proportion of 1000 and 400 mg/kg, respectively, during the trial period (14 d), then receiving MDB according to the invention in a proportion of 2% by weight of the food during the remaining period of the trial (15-77 days).

At the end of the trial, blood samples are taken from 6 piglets per subgroup and the haptoglobin content is determined therefrom (expressed in mg/ml of blood).

The following Table XI gives the results obtained.

TABLE XI

|  | Batch No. 1 | Batch No. 2 | Batch No. 3 | Batch No. 4 |
|---|---|---|---|---|
| Haptoglobin content | 5.74 | 1.83 | 4.45 | 4.36 |

The results show that the blood haptoglobin content of the animals fed with the fiber-enriched anti-inflammatory and analgesic composition for the bowel in accordance with the invention (batch No. 2) is significantly lower than that of the animals having received a conventional diet, which thus reflects a blood, and therefore systemic, inflammation level which is lower than the controls.

In batch No. 4, the result is less than that of the control group, even though it is not significant. This decrease supports, however, the desired effect, namely a lower anti-inflammatory status.

Example 4

The effect of the branched maltodextrins of the invention (those of Example 1) on intestinal fermentations is studied in laboratory rats.

OFA rats of Sprague Dawley origin are divided up into 4 groups which receive in their food intake a diet, the details of which are given in the following Table XII.

Group 4 receives a food intake supplemented with fructooligosaccharides (Raftilose® P95 sold by the company Orafti).

TABLE XII

| Batch | Food and product tested |
|---|---|
| 1 | Food AO4C |
| 2 | Food AO4C + 10% glucose |
| 3 | Food AO4C + 10% MDB |
| 4 | Food AO4C + 10% Raftilose ® P95 |

After one week of isolation during which the animals receive a standard food intake and drinking water, the rats consume the food for 36 days.

At $D_0$, the animals are made to fast for 24 hours. The drink is given ad libitum. At $D_1$, the feces are collected.

The diet described in Table XII is given to the animals.

At $D_{28}$, the animals are made to fast for 24 h. The drink is given ad libitum.

At $D_{29}$, the feces are again collected.

At $D_{36}$, the animals are sacrificed.

A general macroscopic observation of the organs is carried out. The ceca are ligatured and removed. The full ceca, the cecal contents and the empty ceca are weighed.

The pH and the solids of the feces and of the cecal contents are determined.

The enzymatic activities of the feces are also evaluated ($\alpha$-glucosidase and $\beta$-glucosidase).

The distribution of volatile fatty acids is studied in the cecal content (acetic acid, propionic acid, butyric acid).

The following Table XIII gives the data concerning the weight of the full ceca, the weight of the empty ceca, and the pH of the cecal content (expressed as mean value over 10 animals per batch±standard deviation).

TABLE XIII

| Batch | Weight of the full cecum (g) | Weight of the empty cecum (g) | pH of the cecal content |
|---|---|---|---|
| 1 | 5.64 ± 0.31 | 0.96 ± 0.09 | 6.77 ± 0.28 |
| 2 | 5.78 ± 0.78 | 0.93 ± 0.11 | 6.75 ± 0.18 |
| 3 | 8.29 ± 1.45 | 1.25 ± 0.16 | 6.21 ± 0.16 |
| 4 | 8.68 ± 1.08 | 1.44 ± 0.21 | 6.49 ± 0.20 |

Table XIII shows that the weight of the full and empty ceca are significantly higher for the animals receiving 10% of MDB according to the invention or 10% of Raftilose® P95, in comparison with the animals receiving a standard food intake or one containing 10% of dextrose.

Compared with the control batch, the weight of the full cecum of the animals receiving 10% of MDB increases by 46%, and by 53% for the animals receiving 10% of Raftilose® P95.

The weight of the empty cecum, for its part, changes by 30% for the batch receiving MDB and by 50% for the batch receiving Raftilose® P95.

These results show that the MDB and the Raftilose® P95 increase the weight of the cecum and therefore of the cecal bacterial mass and also the weight of the cecal mucosa, thus resulting in a physical protection in the face of an inflammation.

This table also shows that there is a significant decrease in the pH of the cecal content for the batch receiving the MDB, thus reflecting a substantial cecal fermentive activity.

This decrease in pH reflects an increase in acidic molecules in favor of a decrease in basic molecules which would be more aggressive in nature.

The Raftilose® P95, for its part, does not exhibit these properties, since the pH of the cecal content does not significantly decrease.

Table XIV gives the data relating to the distribution of the volatile fatty acids of the cecal content.

TABLE XIV

| Batch | Acetic acid (mg/g of the cecal content) | Butyric acid (mg/g of the cecal content) | Propionic acid (mg/g of the cecal content) |
|---|---|---|---|
| 1 | 3.07 ± 0.68 | 2.33 ± 0.97 | 0.75 ± 0.11 |
| 2 | 2.88 ± 0.60 | 1.97 ± 0.63 | 0.76 ± 0.19 |
| 3 | 3.55 ± 0.50 | 2.65 ± 0.67 | 1.56 ± 0.32 |
| 4 | 3.37 ± 0.31 | 2.46 ± 0.56 | 0.99 ± 0.15 |

This table shows that a food intake supplemented with 10% of MDB brings about a significant increase in the propionic acid of the cecal content.

This result is also obtained for the batch receiving Raftilose® P95, but in a less accentuated manner.

No significant difference is apparent for the dosage of acetic acid in the cecal content.

Table XV gives the data relating to the fecal pH.

TABLE XV

| Batch | $D_1$ fecal pH | $D_{29}$ fecal pH |
|---|---|---|
| 1 | 6.38 ± 0.34 | 6.58 ± 0.40 |
| 2 | 6.34 ± 0.34 | 6.59 ± 0.29 |

TABLE XV-continued

| Batch | $D_1$ fecal pH | $D_{29}$ fecal pH |
|---|---|---|
| 3 | 6.37 ± 0.22 | 6.23 ± 0.47 |
| 4 | 6.29 ± 0.40 | 6.23 ± 0.47 |

These results do not make it possible to observe a significant decrease in fecal pH in the animals receiving the MDB, although a decrease in the cecal pH was observed.

On the other hand, the fecal pH decreases for the animals receiving Raftilose® P95.

Tables XVI and XVII give the enzymatic activities of the feces determined at $D_0$ and $D_{29}$, respectively.

TABLE XVI

| Batch | α-glucosidase (Uabs/min/g of feces) | β-glucosidase (Uabs/min/g of feces) |
|---|---|---|
| 1 | 3.23 ± 1.17 | 4.40 ± 2.86 |
| 2 | 3.19 ± 1.72 | 3.86 ± 2.03 |
| 3 | 3.37 ± 1.85 | 2.55 ± 1.11 |
| 4 | 3.10 ± 1.37 | 2.94 ± 1.19 |

At $D_0$, there is of course no significant difference observed between the batches.

TABLE XVII

| Batch | α-glucosidase (Uabs/min/g of feces) | β-glucosidase (Uabs/min/g of feces) |
|---|---|---|
| 1 | 5.62 ± 1.24 | 6.08 ± 1.39 |
| 2 | 5.97 ± 2.60 | 6.74 ± 3.38 |
| 3 | 23.09 ± 7.29 | 24.21 ± 9.10 |
| 4 | 15.32 ± 3.91 | 9.94 ± 3.05 |

At $D_{29}$, the glucosidase activities are greatly increased by the administration of 10% of MDB. This is also the case for the animals receiving 10% of Raftilose® P95, but in a less accentuated manner.

In fact, increases of 310% and of 298% are observed for, respectively, α-glucosidase and β-glucosidase in the batch receiving the MDB compared with the control batch, whereas the increases are only 172% and 63%, respectively, for the Raftilose® P95 batch.

The increases in the glucosidase activities of the feces result in colonic digestion of the polysaccharide residues present.

This high glucosidase activity can thus lead to a decrease in the bioavailability of certain polyphenols (important participants in the repair of a colonic inflammation), and also a decrease in oxidative stress.

Example 5

The effect of the branched maltodextrins of the invention (identical to those of Example 1) on the production of butyric acid is studied in laboratory rats.

18 Fischer laboratory rats are divided up into 3 groups which receive, in their food intake, a diet given in the following Table XVIII.

Group 3 receives a food intake supplemented with fructooligosaccharides (Actilight® sold by the company Beghin-Meiji).

TABLE XVIII

| Batch | Food and product tested |
|---|---|
| 1 | Food AO4C |
| 2 | Food AO4C + 5% MDB |
| 3 | Food AO4C + 5% of Actilight ® |

After one week of quarantine during which the animals receive a standard food intake and drinking water, the rats consume the food stated in Table XVIII for 14 days.

At $D_{14}$, the animals are sacrificed. A general macroscopic observation of the organs is carried out. The ceca are ligatured and removed.

The distribution of volatile fatty acids in the cecal content is studied.

The following Table XIX gives the results obtained for butyric acid.

TABLE XIX

| Batch | Butyric acid (mg/cecum) |
|---|---|
| 1 | 12.6 ± 2.5 |
| 2 | 17.5 ± 3.0 |
| 3 | 16.3 ± 3.8 |

The amount of cecal butyric acid increases for the animals having received MDB, which can thus be categorized among the butyrogenic glucidic substrates in animals.

Butyric acid is an important factor for cell growth and differentiation, thereby justifying the protective action of the MDB against inflammations of the colon.

Example 6

The effect of the branched maltodextrins of the invention (identical to those of Example 1) and of dextrose (control) on the production of various cell receptors involved in bowel inflammation and analgesia is studied in laboratory mice.

20 7-week-old Balb/c mice are divided up into 2 groups.

One group receives drink consisting of a solution of 10% of dextrose in drinking water, the other group receives a solution of 10% of MDB in drinking water.

The animals receive an unlimited supply of this drink and standard mouse food for 29 days.

At $D_{29}$, the mice are sacrificed and the colon is removed and analyzed for the following markers:
peroxisome proliferator-activated receptors (PPARγs)
μ opioid receptor (MOR).

In order to evaluate the role of the branched maltodextrins of the invention in the physiological regulation of inflammation, the total RNAs of the removed colons are isolated using the NucleoSpin® RNA II kit sold by the company Clontech Laboratories Inc. The total RNAs are reverse transcribed to cDNA using reverse transcriptase.

The reverse transcription reaction is amplified and quantified by real time PCR (Applied Biosystems) using a primer for PPARγ and MCR. The results are expressed in numbers of mRNA molecules per mRNA molecule of the internal β-actin control.

The following Table XX gives the means of the results obtained following the assaying of the PPARγs and of the MORs in the colonic mucosa of the rats.

TABLE XX

| PPARγ | | MOR | |
|---|---|---|---|
| Control batch 10% Dextrose (n = 6) | Treated batch 10% MDB (n = 8) | Control batch 10% Dextrose (n = 7) | Treated batch 10% MDB (n = 9) |
| 5.02 ± 1.65 | 8.64 ± 2.42 | 0.98 ± 0.70 | 4.34 ± 3.02 |

A considerable increase in these two factors is observed with the introduction into the food of 10% of the MDB of the present invention for 29 days:
increase by a factor of 1.72 for the PPARγs
increase by a factor of 4.43 for the MORs.

The results of the batch treated with 10% of the MDB shows significantly greater amounts than the results obtained for the control batch with 10% of dextrose (p<0.03 for the PPARγs and p<0.04 for the MORs).

The MDB of the invention can thus be an aid to the regulation of a possible inflammation by maintaining, in particular, the integrity of the intestinal mucosa.

In fact, the increase in the number of PPARγ molecules indicates that the colon has a better anti-inflammatory status when the animals have consumed MDB.

The increase in the number of MOR pain receptors is, for its part, synonymous with a decrease in visceral sensitivity to pain. These results are entirely consistent with those of Example 2, in which the analgesic role of the MDB had been demonstrated by an effect on the cognitive behavior of the animals.

The invention claimed is:

1. A method for treating bowel inflammations and/or bowel pain caused by inflammation, comprising administering to an individual a sufficient therapeutic amount of a branched maltodextrin having between 15% and 35% of 1->6 glucosidic linkages, a reducing sugar content of less than 20%, a polymolecularity index of less than 5, and a number-average molecular mass Mn at most equal to 4500 g/mol.

2. The method as claimed in claim 1, wherein said branched maltodextrin has a reducing sugar content of between 2% and 5%, and a number-average molecular mass Mn of between 2000 and 3000 g/mol.

3. The method as claimed in claim 1, wherein the branched maltodextrin has a total fiber content of greater than 50% on a dry matter basis.

4. A method for treating bowel inflammations and/or bowel pain caused by inflammation, comprising administering to an individual of a sufficient therapeutic amount of a fiber-enriched composition comprising as active ingredient, branched maltodextrins having between 15% and 35% of 1->6 glucosidic linkages, a reducing sugar content of less than 20%, a polymolecularity index of less than 5, and a number-average molecular mass Mn at most equal to 4500 g/mol.

5. The method as claimed in claim 4, wherein the fiber-enriched composition comprises 0.5% to 20% by dry weight of said branched maltodextrins.

6. The method as claimed in claim 4, wherein the fiber-enriched composition is in the form of a drink, a soup or a yogurt or is incorporated into breakfast cereals.

7. The method as claimed in claim 4, wherein the fiber-enriched composition also comprises at least one active ingredient chosen from the group consisting of sulfasalazine, 5-aminosalicylates and corticoids.

8. The method as claimed in claim 4, wherein the fiber-enriched composition also comprising an active ingredient chosen from the group consisting of sulfasalazine and 5-aminosalicylates, characterized in that the ratio by weight of branched maltodextrins to weight of sulfasalazine or of one of its derivatives is between 2 and 30.

9. The method as claimed in claim 4, wherein the fiber-enriched composition also comprising an active ingredient chosen from the group consisting of corticoids, characterized in that the ratio by weight of branched maltodextrins to weight of corticoids is between 2 and 250.

10. The method as claimed in claim 7, wherein the fiber-enriched composition is in the form of a liquid, a powder, a syrup, a suppository, a tablet or a lozenge.

11. A kit for the therapeutic treatment of bowel inflammation and/or bowel pain caused by inflammation, comprising:
    a) a fiber-enriched composition comprising as active ingredient, branched maltodextrins having between 15% and 35% of 1->6 glucosidic linkages, a reducing sugar content of less than 20%, a polymolecularity index of less than 5, and a number-average molecular mass Mn at most equal to 4500 g/mol; and
    b) a composition comprising an anti-inflammatory agent for the bowel in a sufficient therapeutic amount to treat bowel inflammation and/or bowel pain caused by inflammation.

12. The method as claimed in claim 2, wherein the branched maltodextrin has a total fiber content, determined according to AOAC method No. 2001.03, of greater than 50% on a dry matter basis.

13. A method for treating bowel inflammations and/or bowel pain caused by inflammation, comprising administering to an individual a sufficient therapeutic amount of a fiber-enriched composition, wherein the fiber-enriched composition comprises, as active ingredient, a branched maltodextrins having between 15% and 35% of 1->6 glucosidic linkages, a reducing sugar content of less than 20%, a polymolecularity index of less than 5, and a number-average molecular mass Mn at most equal to 4500 g/mol and a reducing sugar content of between 2% and 5%, and a number-average molecular mass Mn of between 2000 and 3000 g/mol.

14. A method for treating bowel inflammations and/or bowel pain caused by inflammation, comprising administering to an individual a sufficient therapeutic amount of a fiber-enriched composition, wherein the fiber-enriched composition comprises, as active ingredient, a branched maltodextrins having between 15% and 35% of 1->6 glucosidic linkages, a reducing sugar content of less than 20%, a polymolecularity index of less than 5, and a number-average molecular mass Mn at most equal to 4500 g/mol and a total fiber content, determined according to AOAC method No. 2001.03, of greater than 50% on a dry matter basis.

15. The method as claimed in claim 5, wherein the fiber-enriched composition is in the form of a drink, a soup or a yogurt or is incorporated into breakfast cereals.

16. The method as claimed in claim 5, wherein the fiber-enriched composition also comprises at least one active ingredient chosen from the group consisting of sulfasalazine, 5-aminosalicylates and corticoids.

17. The method as claimed in claim 5, wherein the fiber-enriched composition also comprising an active ingredient chosen from the group consisting of sulfasalazine and 5-aminosalicylates, characterized in that the ratio by weight of branched maltodextrins to weight of sulfasalazine or of one of its derivatives is between 2 and 30.

18. The method as claimed in claim 5, wherein the fiber-enriched composition also comprising an active ingredient chosen from the group consisting of corticoids, characterized in that the ratio by weight of branched maltodextrins to weight of corticoids is between 2 and 250.

19. The method as claimed in claim 8, wherein the fiber-enriched composition is in the form of a liquid, a powder, a syrup, a suppository, a tablet or a lozenge.

20. The method as claimed in claim 9, wherein the fiber-enriched composition is in the form of a liquid, a powder, a syrup, a suppository, a tablet or a lozenge.

21. A method for treating bowel inflammations and/or bowel pain caused by inflammation, comprising administering to a subject in need thereof the two compositions described in the kit of claim 11, concomitantly or sequentially over time.

22. A pharmaceutical composition for treating bowel inflammations and/or bowel pain caused by inflammation, comprising branched maltodextrins having between 15% and 35% of 1->6 glucosidic linkages, a reducing sugar content of less than 20%, a polymolecularity index of less than 5, and a number-average molecular mass Mn at most equal to 4500 g/mol and at least one active ingredient chosen from the group consisting of sulfasalazine, 5-aminosalicylates and corticoids.

23. The pharmaceutical composition of claim 22 wherein the ratio by weight of branched maltodextrins to weight of the at least one active ingredient is of between 2 and 30 when the active ingredient is sulfasalazine or 5-aminosalicylates and of between 2 and 250 when the active ingredient is corticoid.

24. The method as claimed in claim 4, wherein the fiber-enriched composition comprises 5% to 10% by dry weight of said branched maltodextrins.

* * * * *